United States Patent [19]

Svensson

[11] 4,306,705
[45] Dec. 22, 1981

[54] SLIDE VALVE AND COUPLER ASSEMBLY

[76] Inventor: Jan A. Svensson, Solhemsgatan 12, S-561 35 Huskvarna, Sweden

[21] Appl. No.: 166,943

[22] Filed: Jul. 8, 1980

Related U.S. Application Data

[63] Continuation-in-part of Ser. No. 5,427, Jan. 22, 1979, abandoned.

[51] Int. Cl.³ .............................................. F16K 3/00
[52] U.S. Cl. .................................. 251/149.9; 251/148; 251/329; 128/274; 128/275
[58] Field of Search ...................... 251/148, 152, 149.9; 251/326, 328, 329; 128/274, 275, 295

[56] References Cited

U.S. PATENT DOCUMENTS

| | | | |
|---|---|---|---|
| 2,626,820 | 1/1953 | Dons et al. | 251/152 |
| 2,823,887 | 2/1958 | Osinski | 251/148 |
| 3,901,235 | 8/1975 | Patel et al. | 137/855 X |
| 4,089,506 | 5/1978 | Blake | 251/326 X |
| 4,103,712 | 8/1978 | Fletcher | 251/149.9 |
| 4,160,383 | 7/1979 | Rauschenberger | 137/855 X |

Primary Examiner—William R. Cline

[57] ABSTRACT

A slide valve and coupler assembly is provided, for use in carrying body fluids, capable of controlling flow in one line when attached only to that line, and controlling flow in a fluid line connection between two lines when coupled between those two lines.

17 Claims, 22 Drawing Figures

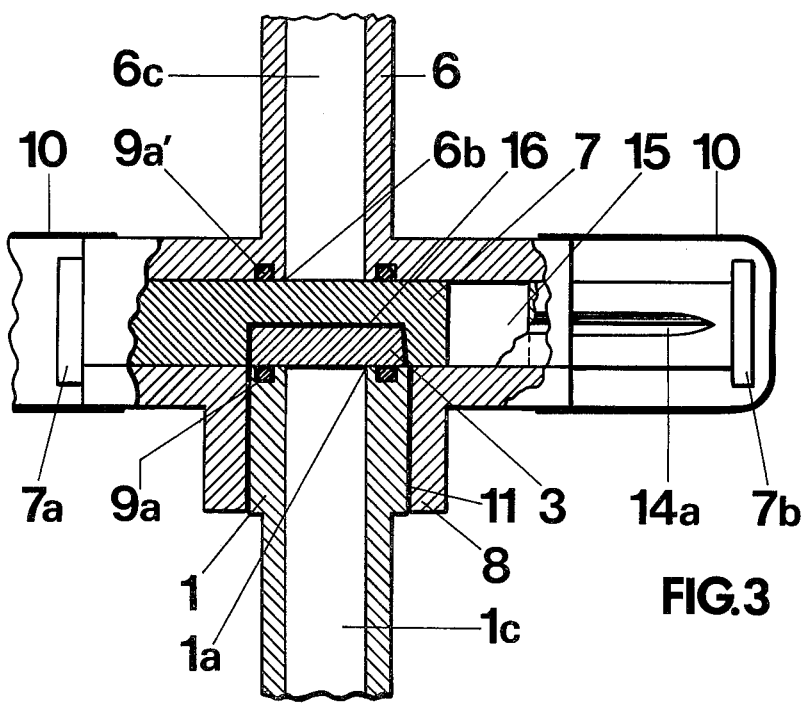
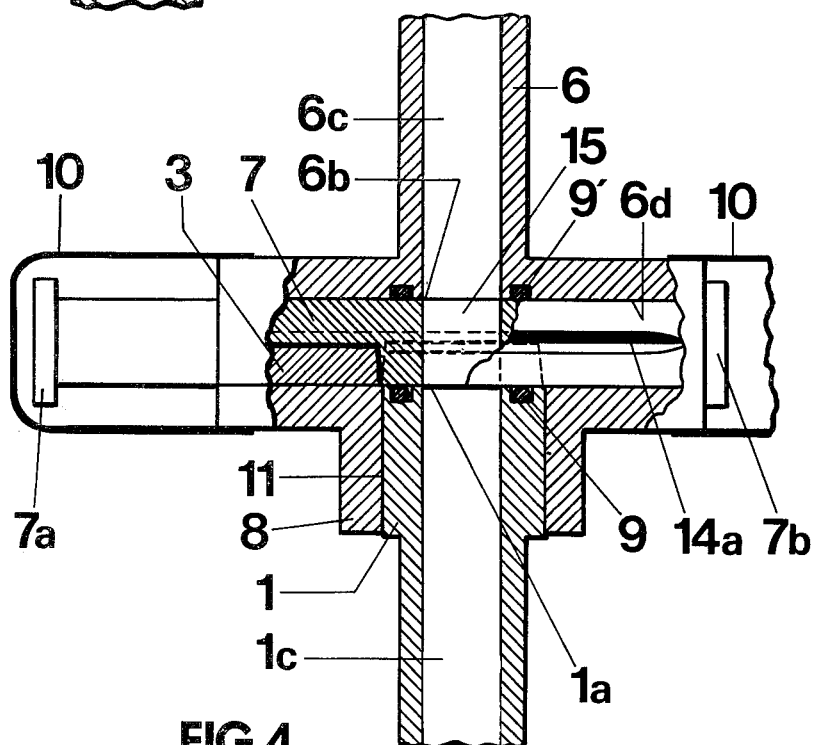

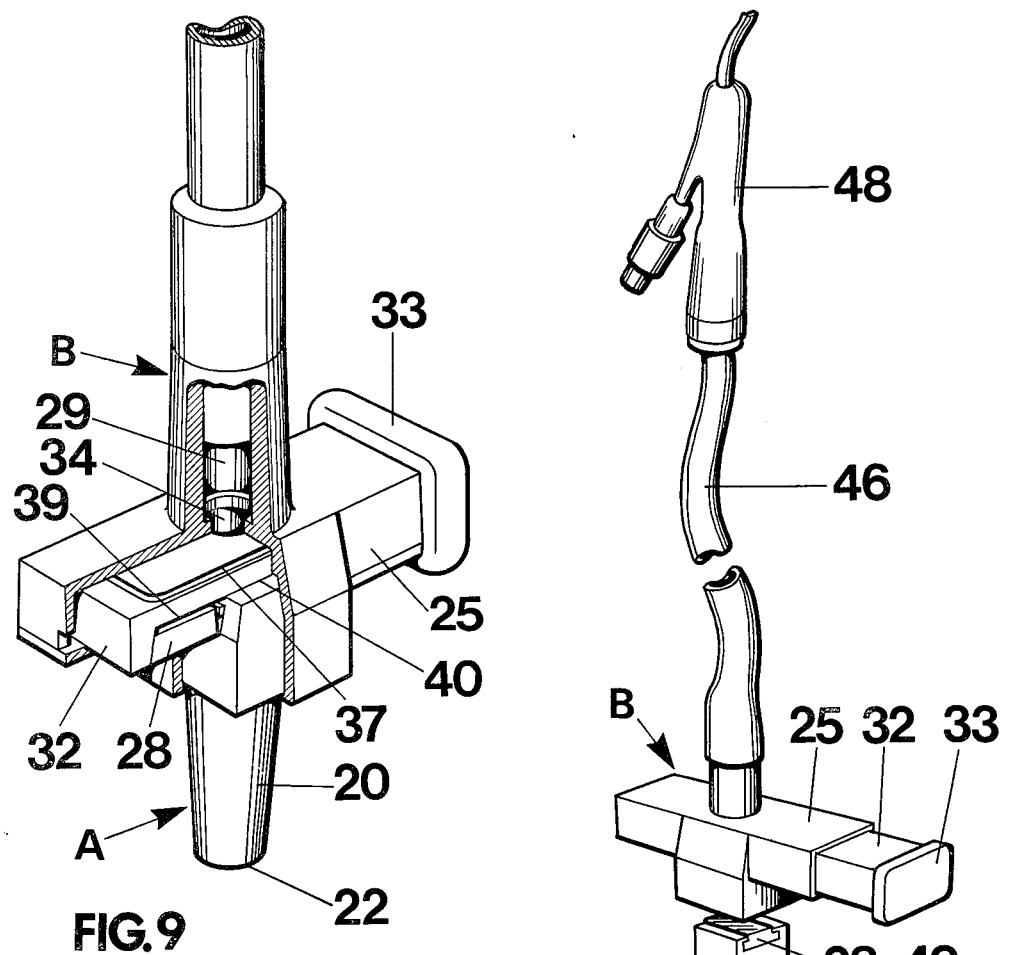
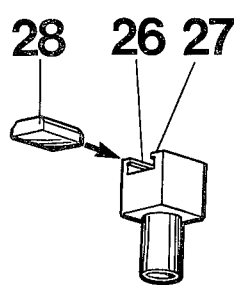
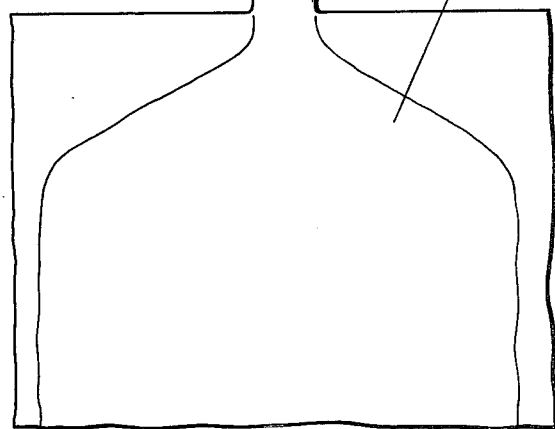
FIG. 9
FIG. 10
FIG. 11

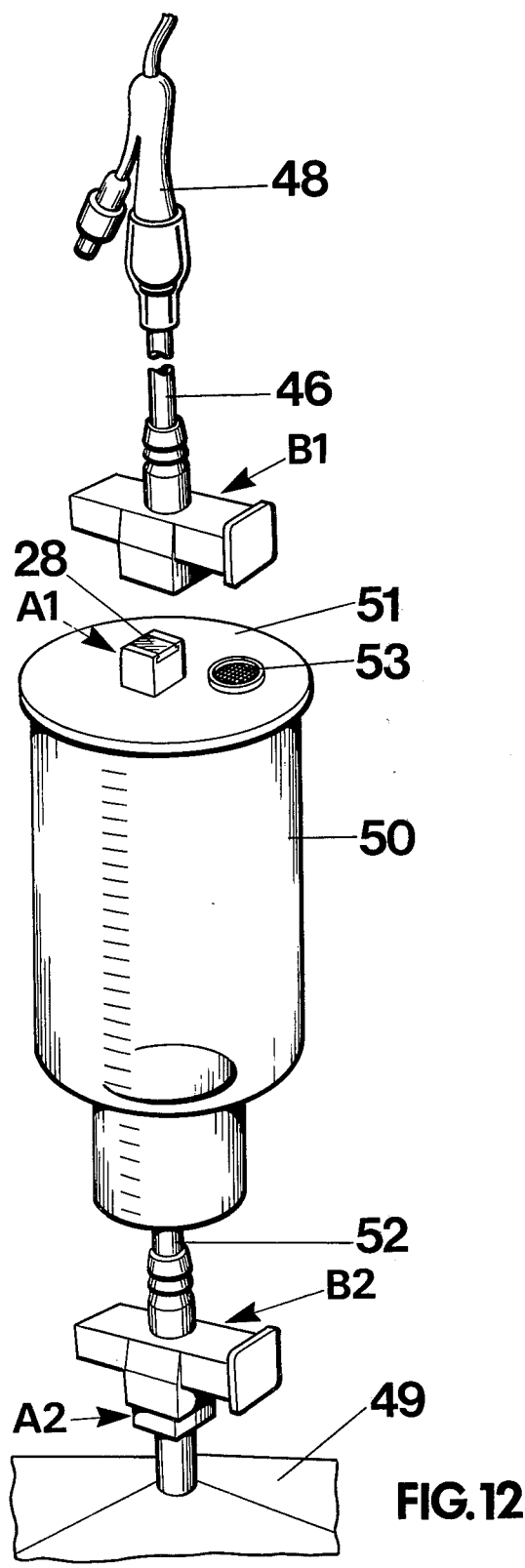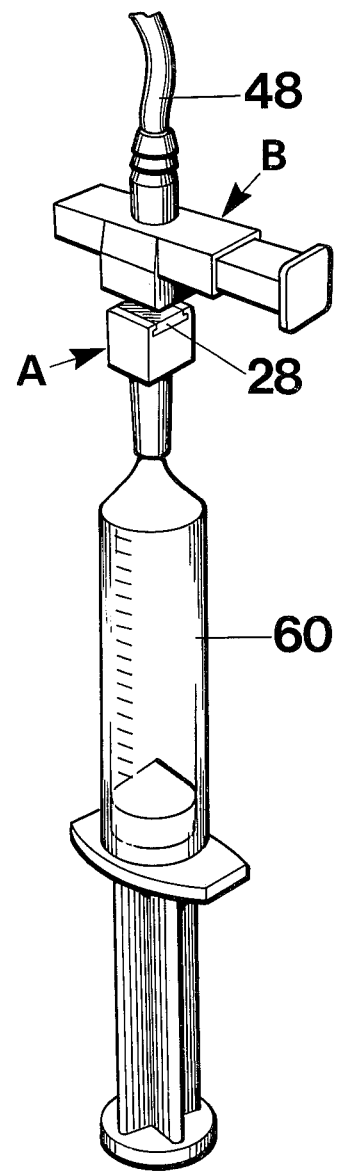
FIG. 12
FIG. 14

SLIDE VALVE AND COUPLER ASSEMBLY

This application is a continuation-in-part of Ser. No. 5,427, filed Jan. 22, 1979, allowed, and now abandoned.

When body fluids are being drained or removed from the body, or medicaments adminstered to the body, it is frequently necessary to disconnect the receptacle in which the fluids are being collected when full, or change the reservoir supplying the medicament, when exhausted. At such times, it is important that the connection to the body be closed, as well as the receptacle, and it is also desirable that the change be made as quickly as possible without spillage or leakage of the fluid and without any risk of bacteria being transferred between the passage for the fluid or medicament and the exterior of the means used for establishing the said connection.

In the collection of urine from incontinent patients in hospitals, it is customary to use a drainage system including a receptacle bag of plastics material, which is suspended at the bed or is carried by the patient; a catheter; and a coupler assembly connecting the receptacle bag to the catheter or to a hose connected with the catheter. The bag is coupled to the catheter or hose in such a way that it can be easily disconnected therefrom when it is necessary to replace the bag; usually about four times each day. When a bag is substantially full, and is to be disconnected from the catheter or hose, the latter is clamped closed upstream of the coupler assembly, and the bag is then disconnected without being sealed at the inlet. Consequently, urine remains in the parts of the coupler assembly associated with the bag and the catheter or hose, with great risk of bacteria transfer and growth during handling and from patients carrying such bags around in the hospital.

The same problems are encountered when the urine is collected in a plastic bag, receptacle or other container having a bottom outlet, and which is emptied periodically through said outlet.

In accordance with the invention, such leakage, bacterial transfer, and spillage are prevented by a slide valve and coupler assembly which controls flow in one line when attached only to that line, and controls flow in a fluid line connection between two lines when coupled between those two lines.

The slide valve and coupler assembly comprises, in combination, (a) a slide valve comprising:
 (1) a valve housing having a fluid inlet and a fluid outlet and means for attaching a first line to one of the inlet and outlet;
 (2) a first fluid flow passage through the housing between the fluid inlet and the fluid outlet;
 (3) at least one slide valve member;
 (4) guide means in the housing for guiding the slide valve member into a position across and closing off the passage to fluid flow, and away from that position leaving the passage open, so that fluid flow can proceed past the valve;
 (5) the slide valve member being carried on and reciprocable into and away from said closed position along said guide means; and (b) a coupler comprising:
 (1) a coupler housing having a fluid inlet and a fluid outlet and means for attaching a second line to one of the inlet and outlet;
 (2) a second fluid flow passage through the coupler housing between the fluid inlet and the fluid outlet;
 (3) a first recess for receiving at least the slide valve member-containing portion of the slide valve housing; the first flow passage through the valve housing and the second flow passage through the coupler housing being in alignment for fluid flow through the assembly when the valve housing is in the first recess;
 (4) at least one second recess abutting and beside the first recess, receiving the slide valve member in an at-rest position away from the flow passage through the slide valve housing;
 (5) operating means for sliding the slide valve member, when the valve housing is inserted in the first recess, between said positions across and closing off the flow passage through the assembly, and away from and opening the flow passsage through the assembly; and
 (6) retaining means on said operating means connecting with the valve housing when the operating means is operated to slide the slide valve member to said opened position and retaining the slide valve to the coupler; whereby the slide valve member controls flow in the first line when the slide valve housing is attached only to that line, and controls flow in the first and second lines when the slide valve housing is inserted in the first recess of the coupler, and the assembly is attached to the first and second lines.

The operating means in the coupler for sliding the slide valve member between the said two positions can be an operating slide controlling flow through the second flow passage in the coupler; and the recess for reception of the slide valve member in the valve housing can be in the operating slide, so that the valve member moves with the operating slide in the coupler assembly between the open and closed positions across and away from the flow passage through the assembly.

The slide valve and coupler assembly of the invention allows connection and disconnection of fluid-carrying parts without communication with the atmosphere and thus prevents bacterial transfer both to the interior of the body and to the surroundings, and thus prevents bacterial transfer in the hospital and the transfer of infections between the patients, to the personnel, and between different wards of the hospital.

The slide valve and coupler assembly of the invention also prevents fluid leakage when receptacles or reservoirs thereof are connected to and disconnected from a body drainage or fluid administration system.

Preferred embodiments of the slide valve and coupler assembly of the invention having a slide valve member in the valve housing and an operating slide in the coupler housing are illustrated in the drawings, in which.

Figure 1:
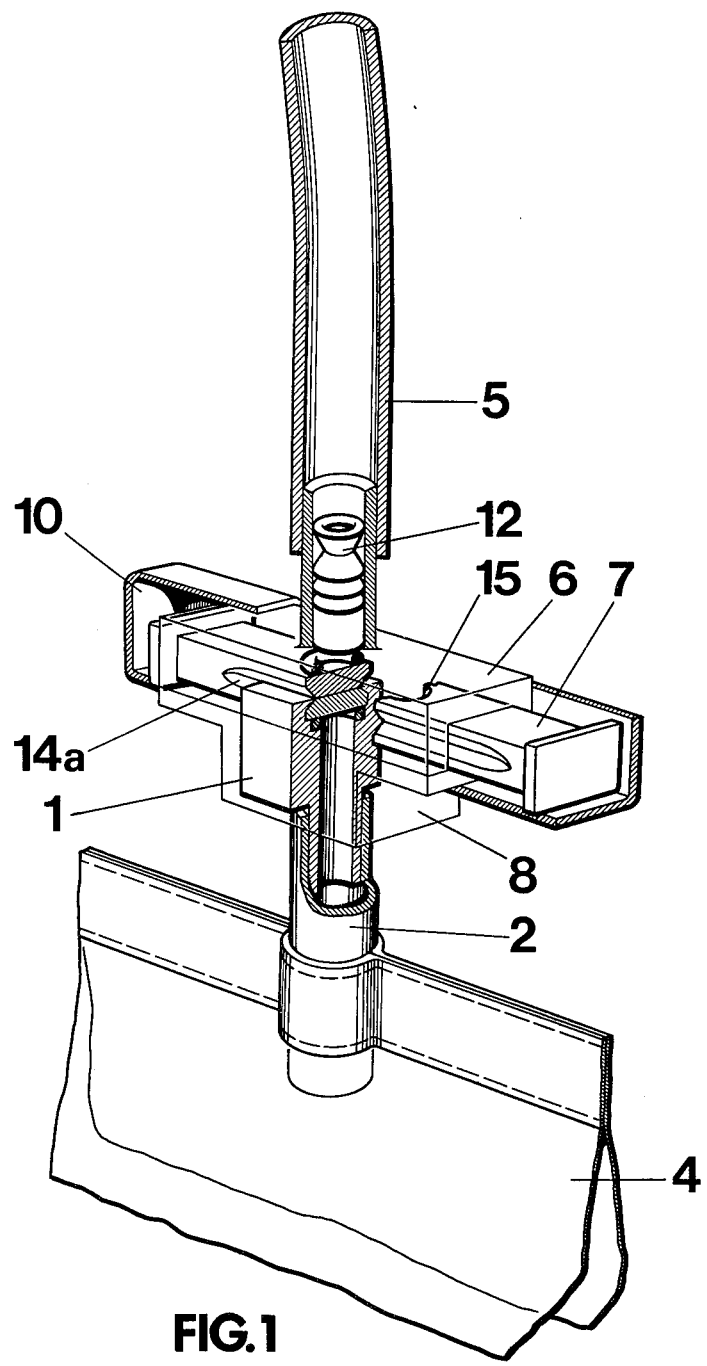
FIG. 1 is a perspective view of the slide valve and coupler assembly, as used in interconnecting a catheter and a receptacle for fluids drained by the catheter.
Figure 2:
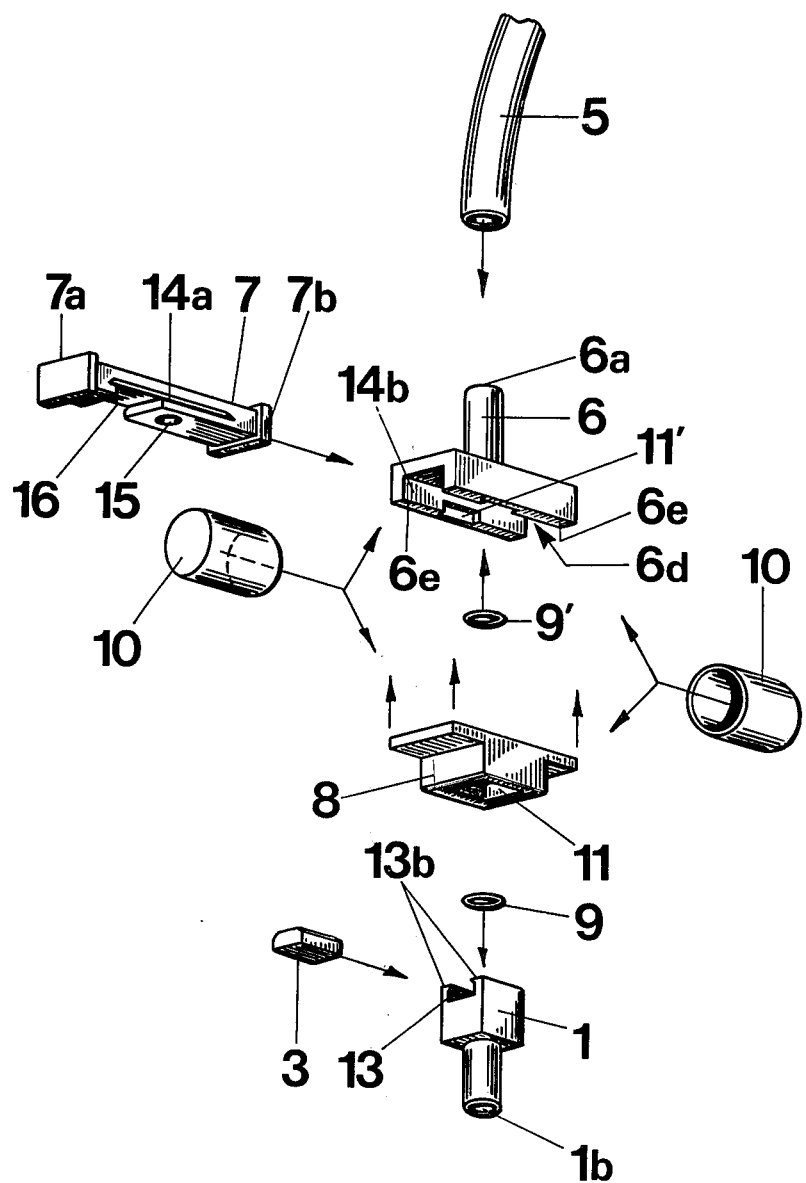
FIG. 2 is an exploded view of the slide valve and coupler assembly of FIG. 1.
Figure 5:
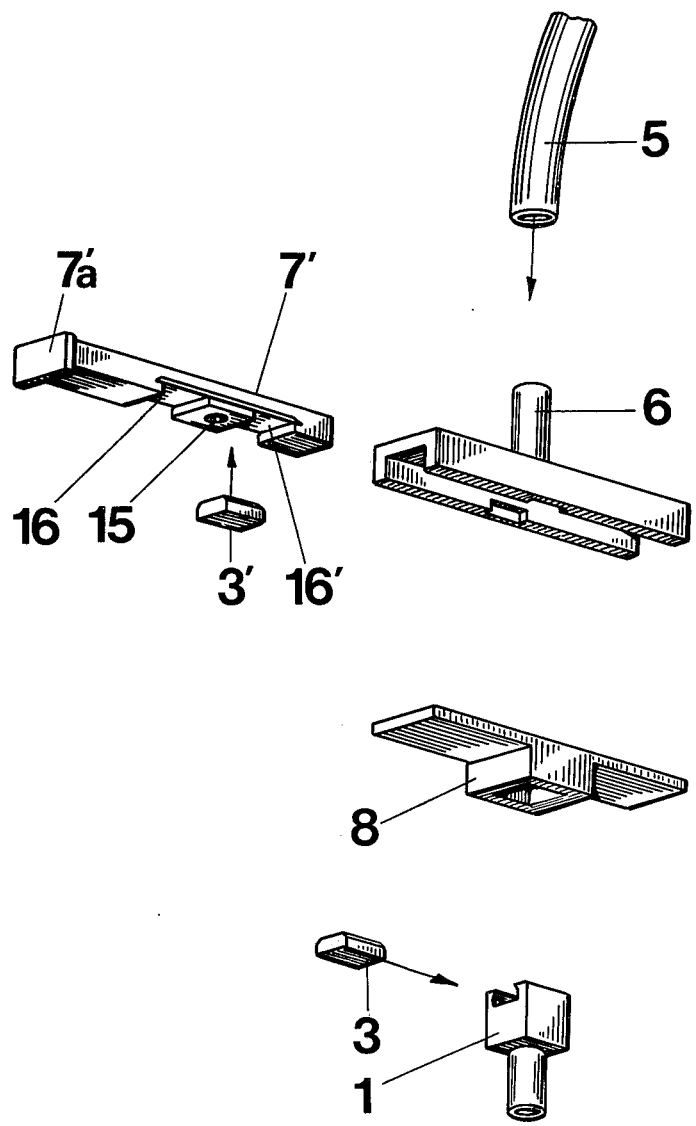

FIG. 3 is a longitudinal sectional view of the slide valve and coupler assembly of FIGS. 1 and 2, showing the slide valve member in the closed position, such as when the slide valve member and valve housing are first installed in the coupler housing; and FIG. 4 is a longitudinal sectional view of the slide valve and coupler assembly, as shown in FIG. 3, but with the slide valve member in the open position, for fluid flow through the coupler assembly;

FIG. 5 is an exploded view of a second embodiment of the slide valve and coupler assembly of the invention having a second slide valve member to be received by the valve housing prior to its removal from the coupler housing.

Figure 6:
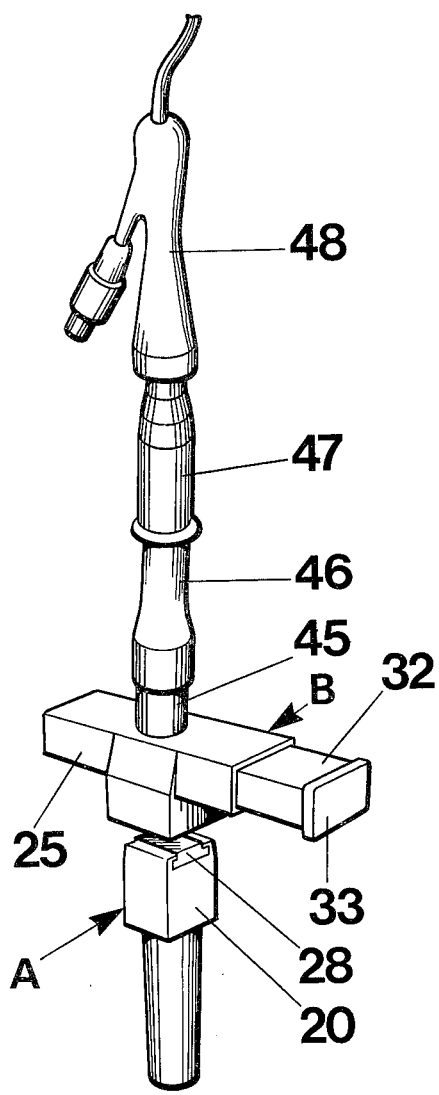
Figure 7:
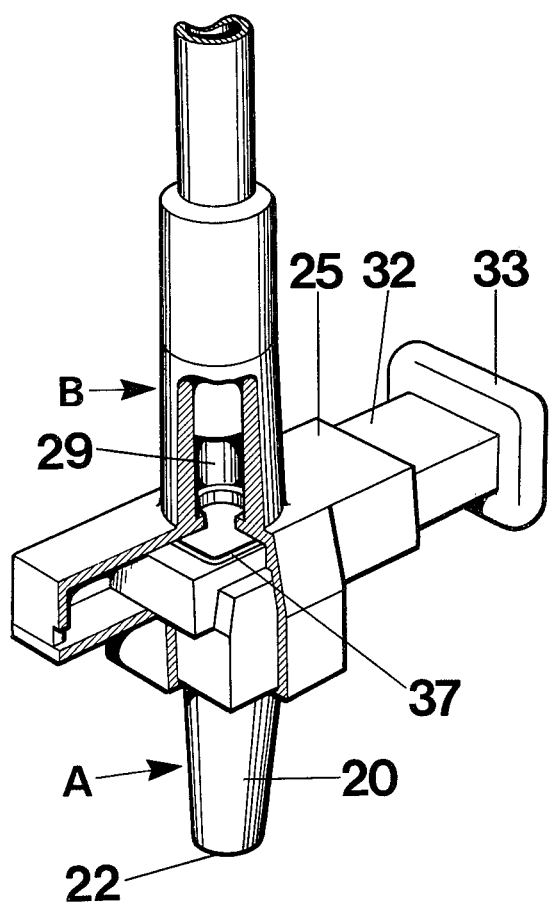
Figure 8:
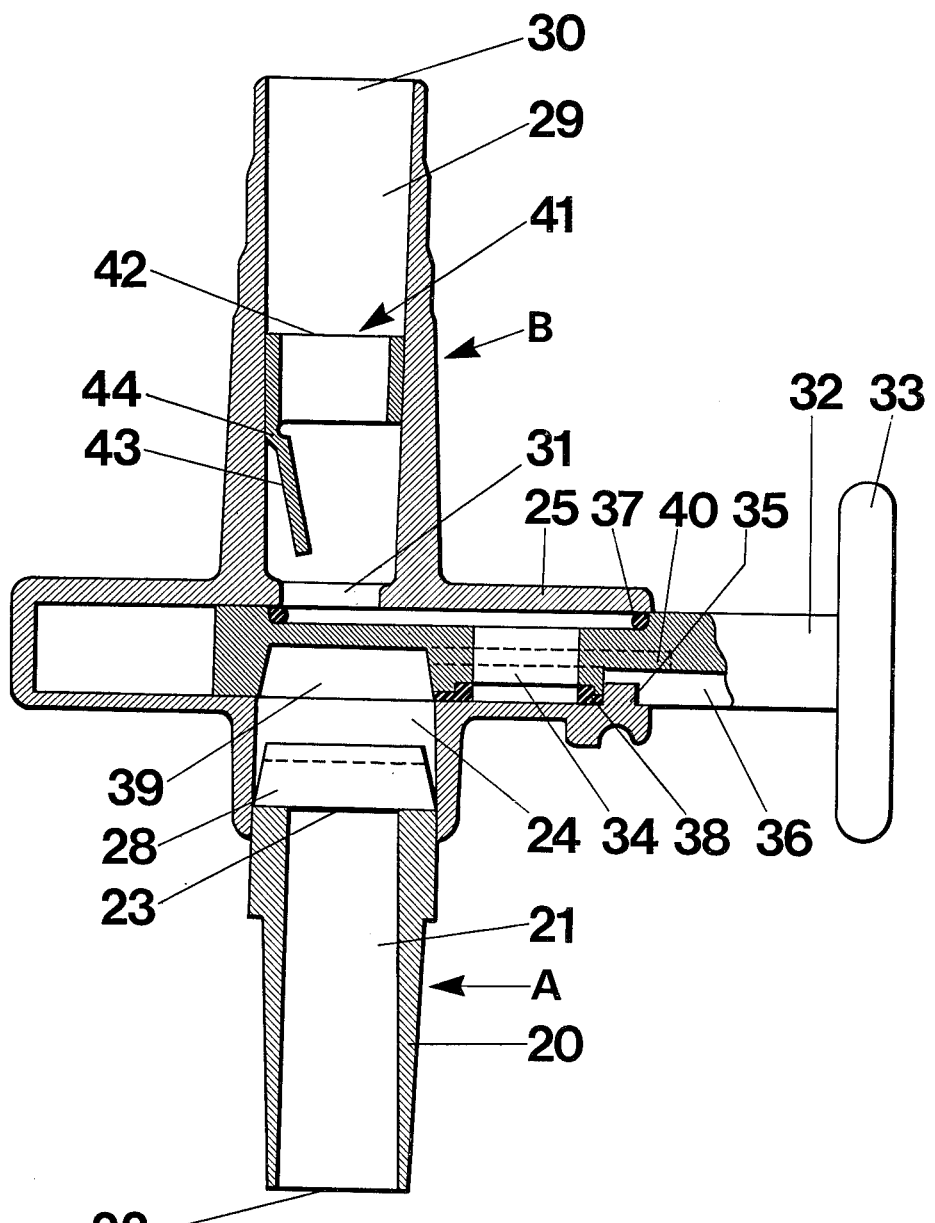

FIG. 6 is a perspective view of another embodiment of slide slide valve and coupler assembly, as used in connection with a catheter, the slide valve and the coupler being shown in disconnected position;

FIG. 7 is a perspective view with parts broken away of the slide valve and coupler assembly of FIG. 6 in the closed position, such as when the slide valve is first installed in the coupler housing;

FIG. 8 is a longitudinal cross-sectional view of the slide valve and coupler assembly of FIGS. 6 and 7 in the closed position, as shown in FIG. 7.

Figure 13:
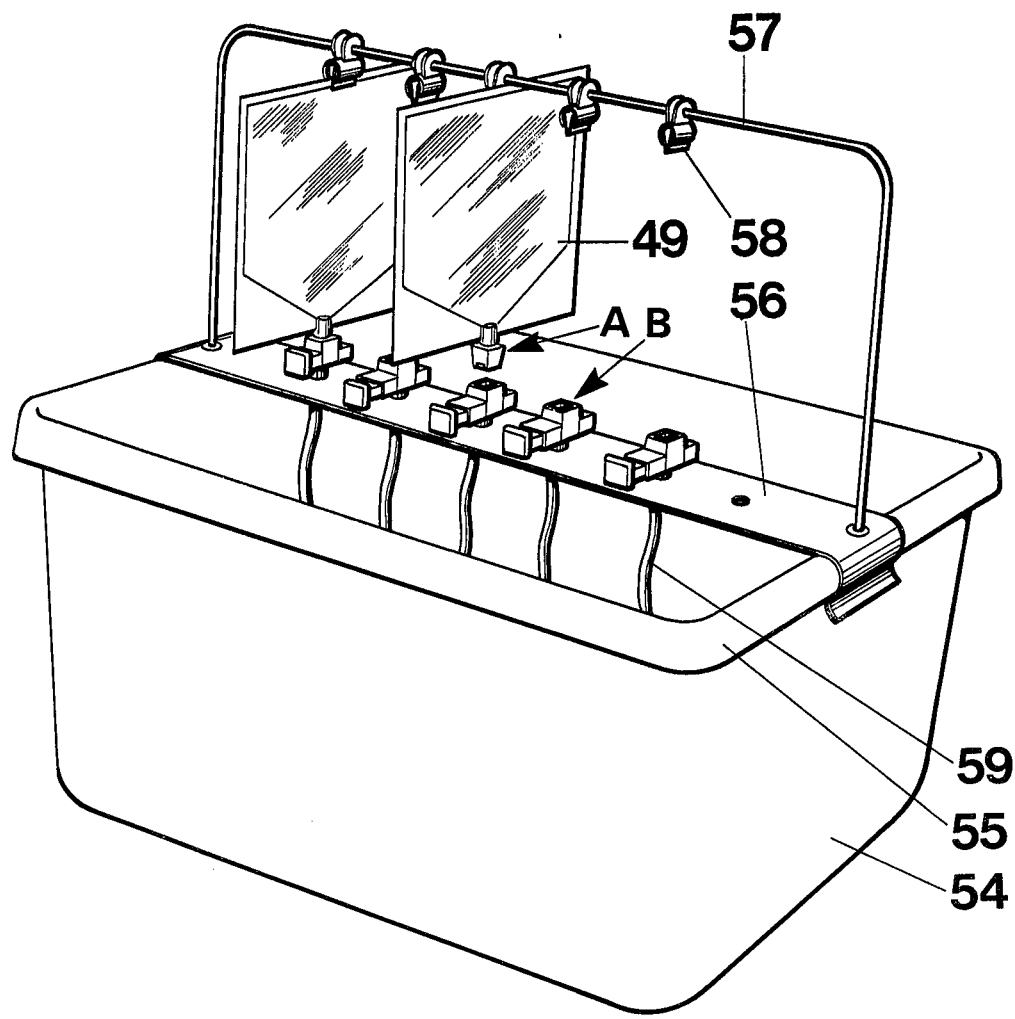
Figure 15:
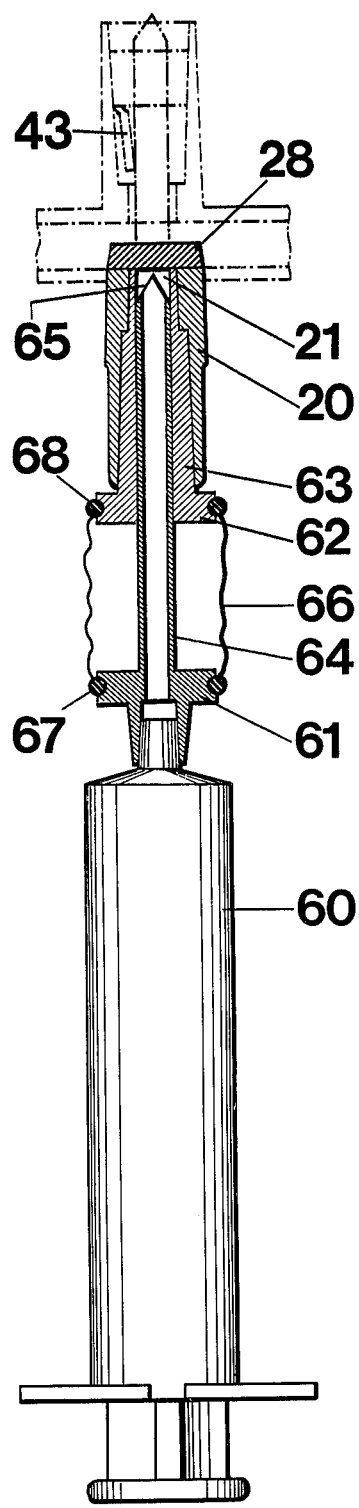
Figure 16:
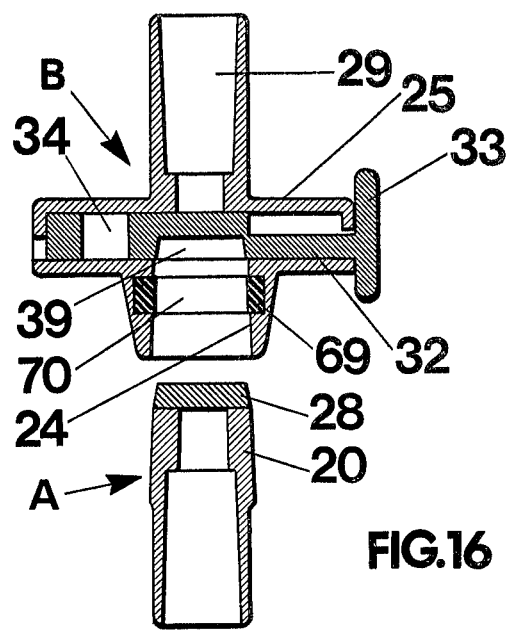
Figure 18:
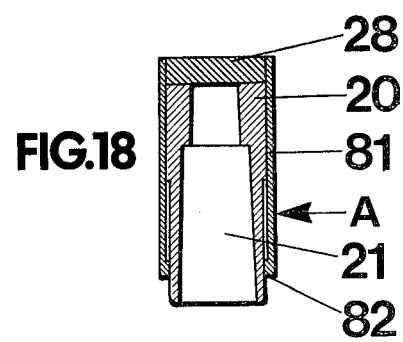
Figure 17:
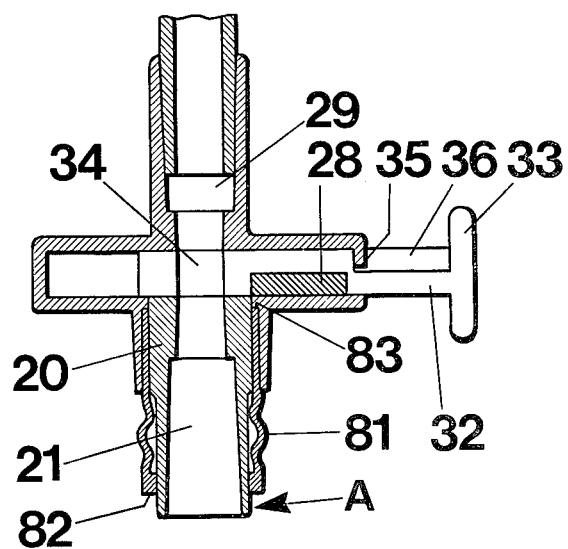
Figure 19:
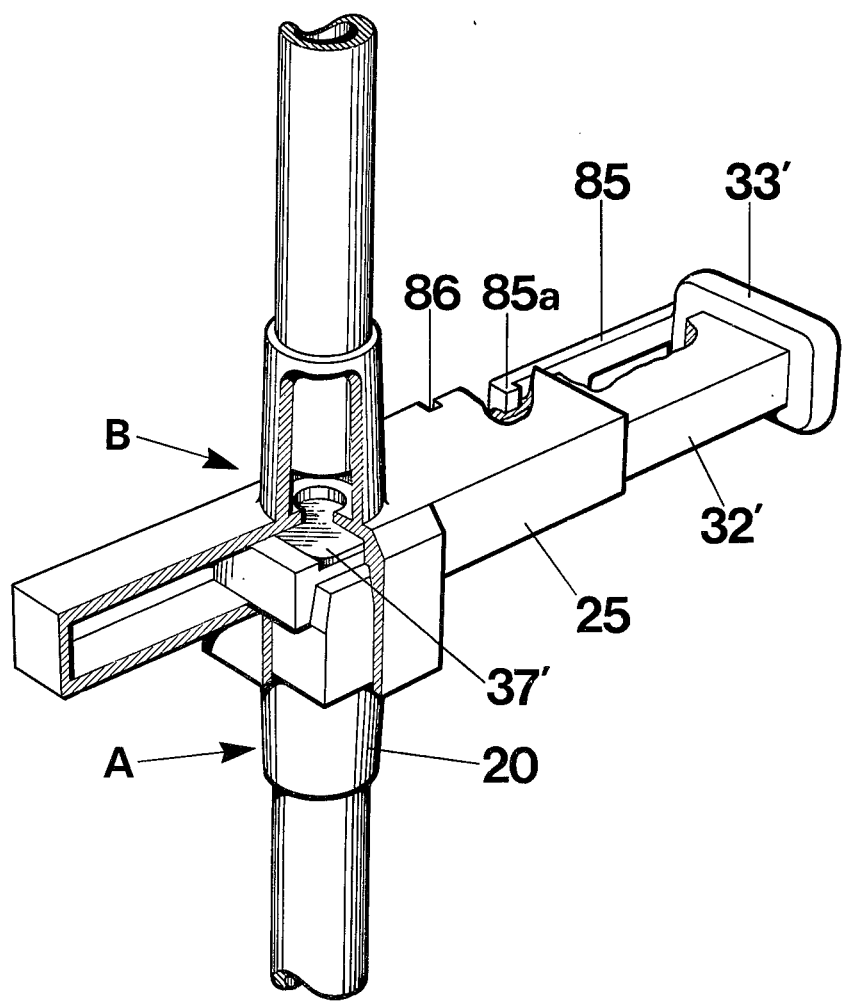
Figure 20:
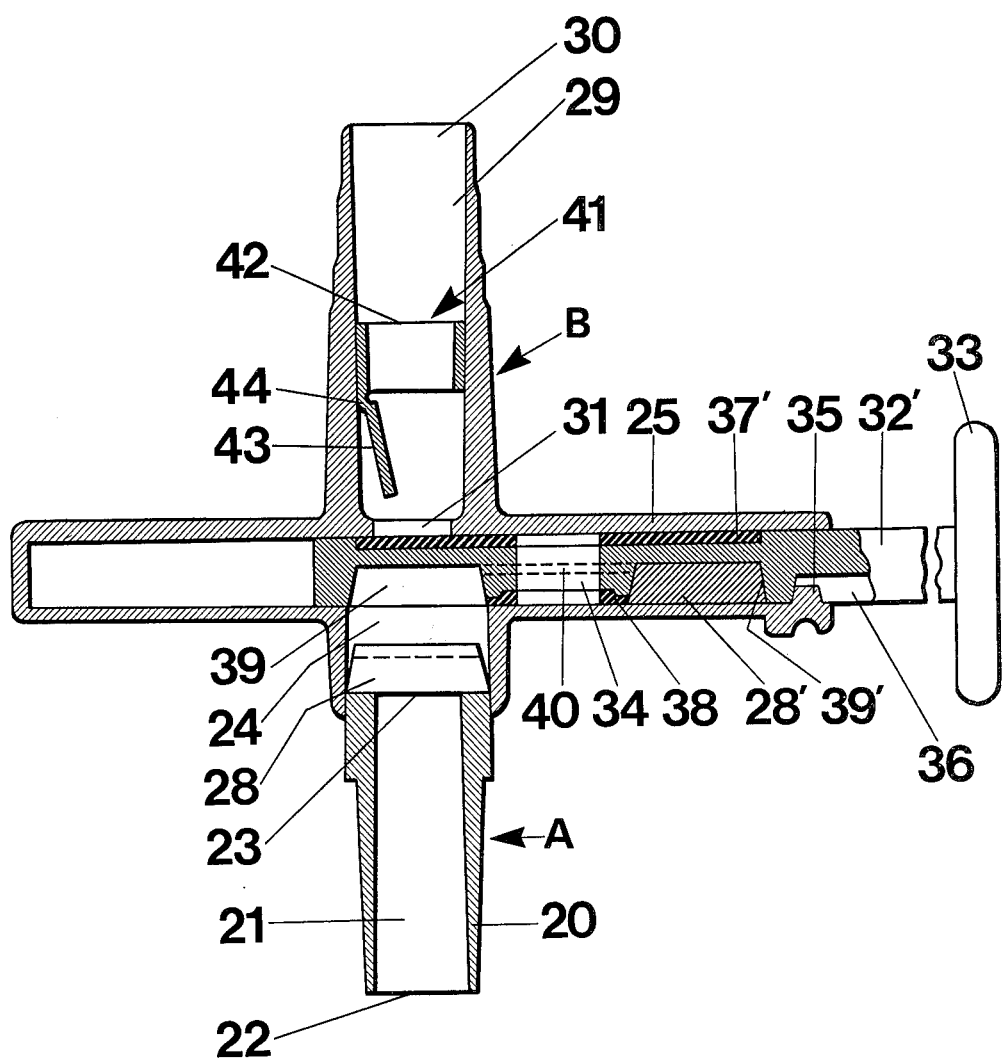
Figure 21:
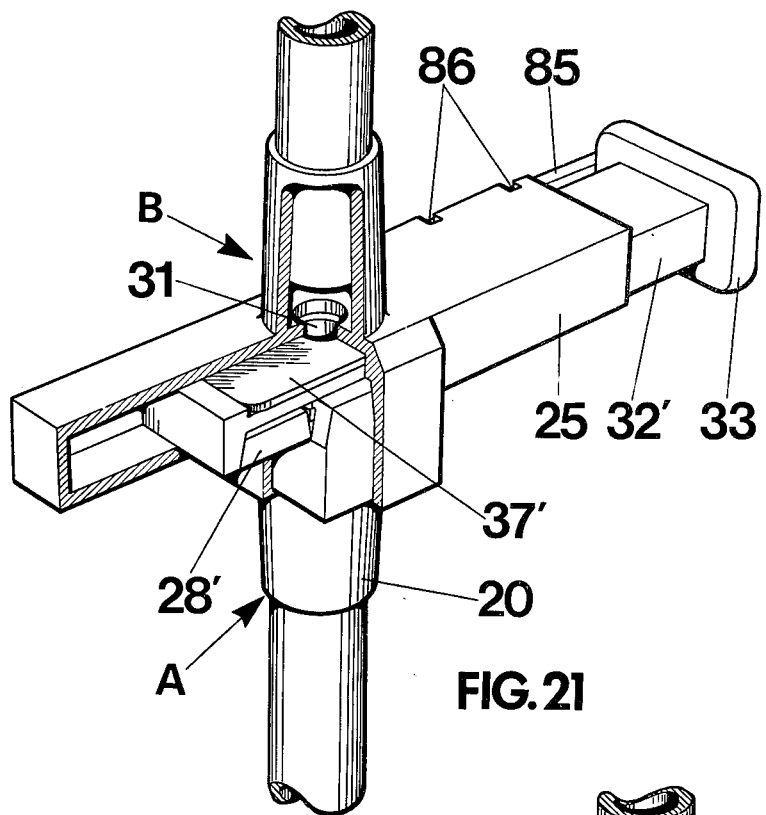
Figure 22:
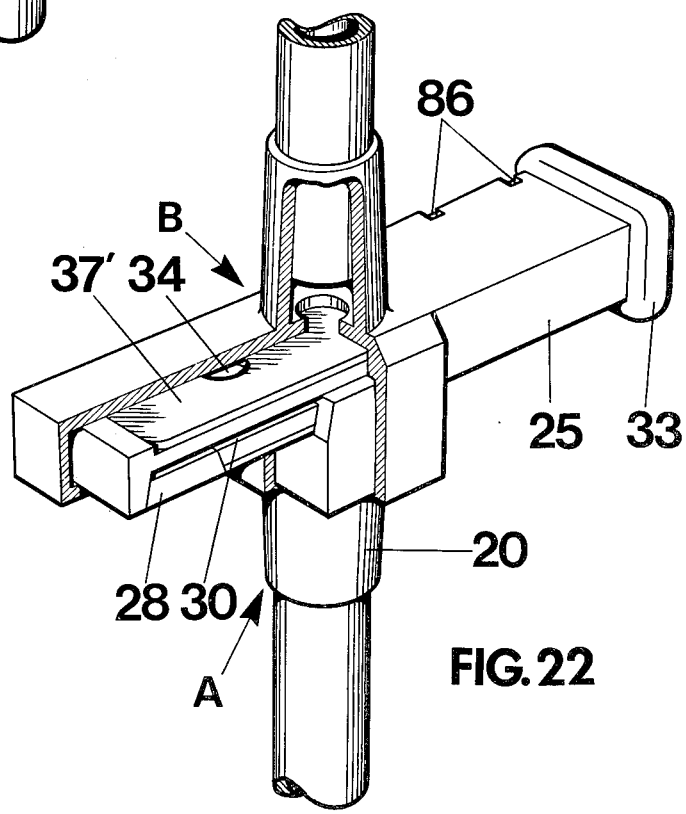

FIG. 9 is a perspective view with parts broken away showing the slide valve and coupler assembly of FIGS. 6 and 7 in the open position, for fluid flow through the assembly;

FIG. 10 is an exploded perspective view of the slide valve of FIGS. 6 and 7;

FIG. 11 is a perspective view of the slide valve and coupler assembly of FIGS. 6 and 7 used in interconnecting a catheter hose and a receptacle for fluids drained by the catheter, the slide valve and coupler assembly being shown in the closed position, with the slide valve disconnected from the coupler housing;

FIG. 12 is a perspective view of the slide valve and coupler assembly of FIGS. 6 and 7 with a fluid measuring apparatus connected therewith;

FIG. 13 is a perspective view of an apparatus for emptying fluid receptacles as that shown in FIG. 11 including a number of couplers according to the invention;

FIG. 14 is a perspective view of the slide valve and coupler assembly of FIGS. 6 and 7 with a syringe connected to the slide valve;

FIG. 15 is a longitudinal cross-sectional view of another embodiment of the slide valve and coupler assembly, with a syringe (shown in elevational side view) connected therewith;

FIG. 16 is a longitudinal cross-sectional view of a further embodiment of the slide valve and coupler assembly, the slide valve and the coupler being shown disconnected from each other;

FIG. 17 is a longitudinal cross-sectional view of the slide valve and coupler assembly of FIG. 16 with the slide valve connected with the coupler;

FIG. 18 is a longitudinal cross-sectional view of a further embodiment of the slide valve and coupler assembly;

FIG. 19 is a perspective view with parts broken away of a further embodiment of the slide valve and coupler assembly, shown in a first closed position;

FIG. 20 is a longitudinal cross-sectional view of the slide valve and coupler assembly of FIG. 19;

FIG. 21 is a perspective view with parts broken away of the slide valve and coupler assembly of FIG. 19, shown in the open position; and FIG. 22 is a perspective view with parts broken away of the slide valve and coupler assembly of FIG. 19, shown in a second closed position.

The slide valve portion of the assembly of FIGS. 1 to 4 has a valve housing 1, with a fluid inlet or outlet port 1a, a fluid outlet or inlet port 1b, and a through flow passage 1c therebetween. The valve housing at the inlet or outlet 1b is shaped to receive a piece of tubing 2 in a snug leak-tight fit. The tubing can lead, for example, to a receptacle 4, as shown in FIG. 1, to a medicament supply container, or simply end in the open air for manual discharge of urine.

In the two embodiments shown, equivalent parts have been given the same reference numerals.

In the embodiment of the invention shown in FIGS. 1 to 4 the valve housing 1 is shaped to fit within the recess 11 of the coupler housing 6. In the portion adjacent the port 1a, the housing is shaped with a reentrant slot 13 having edge portions 13b and serving as a track for the slide valve member 3, along which the valve member can be slid between positions over the port 1a across and away from the through passage 1c. When the slide valve member 3 is in position across the port 1a and passage 1c, the passage is closed. When it is away from the port 1a and passage 1c, the valve member may be out of the slot 13 entirely, whether or not the valve housing 1 is in position in the recess 11 of the coupler housing 6.

It will be noted that the valve member 3 has sides shaped to closely fit within the slot 13. The reentrant configuration of the slot retains the valve member 3 closely against the inner face of the housing 1, and a leak-tight seal at the port 1a is ensured by the seal ring 9, which is received in the recess 9a of the inner face of the housing 1.

The coupler has a coupler housing 6 with an inlet or outlet port 6a, an outlet or inlet port 6b, and a through passage 6c therebetween.

The coupler housing is provided with an operating slide 7, as operating means for movement into and away from a position across and closing off the through passage 6c at the port 6b. The inner face of the housing 6 is channel-shaped, with sides 6e defining a recess 6d for reception of the operating slide 7. The inner face of the housing 6 is provided with a recess 9a', which receives the seal ring 9', engaging (as seen in FIGS. 3 and 4) the adjoining face of the operating slide 7 in a leak-tight seal, when the operating slide 7 is in position across the through passage 6c.

As best seen in FIG. 2, the operating slide 7 has finger rests 7a, 7b at each end, for manual pushing of the slide between its two positions along said recess 6d and peripheral grooves 14a on its sides which engage said edge portions 13b of the reentrant slot 13 in the valve housing 1.

While the recess 6d is open as shown in FIG. 2, it is in fact closed off by the inner face of the housing portion 8, which is normally fixedly attached to the channel sides 6e of housing 6, across the recess 6d, so that the operating slide 7 is permanently retained in the recess.

As seen in FIG. 2, the lower face of the operating slide 7 has a cut-out portion 16, shaped to receive the slide valve member 3 attached to valve housing 1. There is also an aperture 15 corresponding in dimensions and open area to the through passages 1c, 6c of the valve and coupler housings. When the aperture 15 is in register with the passage 6c (and also 1c, if the valve housing 1 is in recess 11), the coupler passage is open to fluid flow, annd when it is not, the coupler passage is closed.

The coupler portion of the assembly of the invention is put together by placing the operating slide 7 in the recess 6d of the coupler housing 6, and then attaching the housing portion 8 to the channel sides 6e so that the operating slide is permanently retained in the recess. The finger rests 7a, 7b which project from the housing on each side of the recess of the operating slide then are covered by the flexible covers 10 which attach to each side of the housing 6 over the recess, so as to aid in preventing the entry of contaminants such as bacteria into the internal portion of the coupler assembly. It is preferred that the covers be of flexible plastic material, so that the operating slide can be pushed to one side or the other without affecting the cover seals. Transparent sheet materials such as polyethylene or polyvinyl chloride are preferred, but other flexible materials, such as natural and synthetic rubbers, can also be used.

The recesses 11, 11', 16 of the valve housing portion 8, the coupler housing 6 and the operating slide 7 are so shaped that the slide valve member 3 fits entirely within the recess 16, and the valve housing 1 in recesses 11 and 11'. The sides of the recess 16 in the operating slide 7 accommodate all of the valve member 3, so as to allow sliding movement of the operating slide 7 therealong. At the same time, with the valve housing 1 in recess 11, the passages 6c, 1c are also in alignment, as is apparent from FIGS. 3 and 4. The side grooves 14a in the operating slide 7 receive the edge portions 13b of the reentrant slot 13 of the slide valve housing, when the operating slide 7 is displaced from the position shown in FIG. 3 to the position shown in FIG. 4, thus acting as locking or retaining means between the coupler housing and the valve housing.

Accordingly, with the operating slide 7 in the position shown in FIG. 3, the slide valve housing 1 with the slide valve member 3 in position closing off the through passage 1c therein can be inserted into the recess 11 in the housing portion 8 of the coupler housing 6 and the slide-valve-member-containing portion of the slide valve housing into the recess 11' in the coupler housing 6. In this position the valve member 3 is in recess 16 of the operating slide 7. In this way, the conduit 2 is put in connection with the coupling unit and conduit 5, while the through passages 6c, 1c are still closed. If now the operating slide 7 is moved to the left into the position shown in FIG. 4, with aperture 15 in alignment with passage 6c, not only does the operating slide 7 itself expose the port 6b and open the through passage 6c, but it also carries with it the slide valve member 3 retained in the recess 16, and opens the port 1a leading to passage 1c in the slide valve housing 1, with the result that the through passages 1c, 6c through the slide valve and coupler assembly are both opened, putting conduit 5 into fluid flow communication with conduit 2.

When the fluid flow connection thus provided is to be interrupted, the operating slide 7 is returned to the position shown in FIG. 3. This closes off both the port 6b and port 1a by the operating slide 7 and the valve member 3, respectively. Now, inasmuch as passages 6c, 1c are closed, it is possible to withdraw the slide valve housing 1 from the recess 11, carrying with it the slide valve member 3, and the receptacle or medicament supply can then be changed without leakage or spillage.

The connection and disconnection of the valve housing to and from the coupler housing can be accomplished without contaminating a sterile environment since no parts or surfaces of the coupling members in contact with fluids passing through the assembly will be exposed to the environment.

A slide valve and coupler assembly according to the present invention on the other hand advantageously can be used in connecting coupling members carrying and transferring other fluids than body fluids, e.g., sterilized fluids.

In FIG. 5 a second preferred embodiment of the coupler assembly according to the present invention is shown.

The operating slide 7' has a second recess 16' with a second valve member 3' on the opposite side of the aperture 15. The operating slide 7' has one finger rest 7'a only, which can be engaged to displace the operating slide from a first position, wherein the valve housing 1 is inserted in the recess 16, to a second position, wherein the passage through the assembly is established, and finally to a third position, wherein the second valve member 3' is displaced to and closes off the opening through the valve housing. In this last position the valve housing 1 can be removed from the coupler housing with the slide valve member 3' connected therewith.

The material of which the operating slide and the valve member are made is resilient and ensures a fluid-tight seal against the valve housing and the coupler housing, also during displacement of the operating slide and the valve members received therein.

The second embodiment of the coupler assembly according to the present invention is used when there is a rigorous requirement for a sterile environment during connection and disconnection of the coupling members. The operating slide 7' and the coupler housing 6 accordingly are used only once to ensure the maintenance of said sterile environment. The valve housing 1 with valve member 3 and the coupler housing 6 with valve member 3' and operating slide 7' can be manufactured and delivered enclosed within sterile housings or covers.

It will be apparent that the coupler 6 can be attached to the body, or to a receptacle, or to a source of supply for a medicament, or the like, and, similarly, the conduit 2 can be so connected. However, one of the two conduits will normally be connected to the body and the other to the receptacle or supply source. For convenience, it is normally preferable that the coupler body 6 be attached to the conduit leading to or from the body, and the valve housing 1 be attached to the receptacle or supply source.

To restore the flexibility of a urine bladder after an operation or otherwise, the normal function of the bladder can be imitated, that is, a discharge of urine from the bladder is performed when the bladder is expanded and contains a collected volume of urine.

An exercise of the bladder to restore its flexibility can be accomplished by using a coupler assembly according to FIGS. 1 to 4.

To the valve housing 1 a piece of tubing 2 is connected. When a discharge of urine is necessary, this piece of tubing 2 is inserted in the coupler housing 6, the operating slide 7 is displaced to move the valve member 3 from the opening 1a in the valve housing 1 to establish a passageway between the conduit 5 and the piece of tubing 2 to lock the valve housing 1 to the coupler housing. The piece of tubing is manually handled during the discharge of urine, which can be accomplished in an almost natural way. After discharge of urine the valve housing 1 with reset slide valve member 3 and piece of tubing 2 is disconnected from the coupler housing and thrown away. The discharge of urine can be performed in a fully satisfactory hygienic way.

In the arrangement shown in FIGS. 1 to 4, the catheter is connected to a drip chamber 12 provided with a bacteria barrier. The drip chamber 12 is contained within the coupler housing 6, and is closed off by the operating slide 7. It will however be apparent that the coupler housing 6 can equally well be connected to any other conduit, and need not include the bacteria barrier and/or drip chamber.

The slide valve and coupler assembly shown in FIGS. 6 to 10 has a slide valve A and a coupler B. The slide valve housing 20 has a through fluid flow passage 21 forming a fluid inlet or outlet port 22 at one end thereof and a fluid outlet or inlet port 23 at the other end thereof. The valve housing is shaped to receive a piece of tubing in a snug leak-tight fit, by which the passage 21 can be connected to a receptacle or other appliance at the outlet or inlet 22. However, the valve housing 20 can also form part of a receptacle or other appliance, or can simply end in the open air, for manual discharge of urine, as shown in FIGS. 6 to 10.

The valve housing 20 is shaped to fit within a recess 24 of a coupler housing 25 forming part of the coupler B. In the portion adjacent to the port 23, the housing is shaped with a reentrant slot 26, FIG. 10, having edge portions 27 and serving as a track for a slide valve member 28, along which the valve member can be slid between closed and open positions over the port 23, across and away from, respectively, the through passage 21. When the slide valve member 28 is in a position across the port 23 and passage 21, the passage is closed. When it is away from the port 23 and passage 21, the passage is open. In this position, the valve member 28 may be out of the slot 26 entirely, whether or not the valve housing 20 is in position in the recess 24 of the coupler housing 25.

It will be noted that the valve member 28 has sides shaped to closely fit within the slot 26. The reentrant configuration of the slot retains the valve member 28 closely against the inner face of the housing 20, and a leak-tight seal at the port 23 is ensured by the valve member 28 being made of resilient rubber or rubber-like plastic material and engaging the bottom surface of the slot 26. However, the valve member 28 can also be made of a substantially rigid material, a sealing ring then being provided in the bottom of the groove 26 around the port 23 of the fluid flow passage 21.

The coupler housing 25 has a through fluid flow passage 29 forming an inlet or outlet port 30 and an outlet or inlet port 31 at the ends thereof. The coupler housing is provided with an operating slide 32 forming a finger rest 33 at one end thereof. There is a through aperture 34 in the operating slide 32, and the slide is guided for displacement in the coupler housing 25 between a first position shown in FIGS. 7 and 8 in which the aperture 34 is away from the port 31 and the coupler passage 29 accordingly is closed by the operating slide, and a second position, shown in FIG. 9, in which the aperture 34 is in register with the port 31 and the coupler passage 29 accordingly is open to fluid flow. The first and second positions are determined by a protrusion 35 formed by the coupler housing 25 and engaging a longitudinal groove 36 in the operating slide 32.

The operating slide 32 is provided with a rectangular sealing ring 37 in the side facing the port 31, and this sealing ring surrounds the port and the aperture 34 in the first and second positions of the operating slide and every position therebetween. On the opposite side of the operating slide 32, facing the recess 24, a sealing element 38 is provided which surrounds the aperture 34.

The lower face of the operating slide 32 has a cut-out portion 39 shaped to receive the slide valve member 28 attached to the valve housing 20.

The slide valve A and the coupler B of the assembly of the invention are put together by placing the operating slide 32 in the first position shown in FIGS. 7 and 8, and then inserting the slide valve into recess 24, the slide valve member 28 being received by the cut-out portion 39 in the operating slide 32. In this position of the slide valve in the coupler housing, longitudinal side grooves 40 in the operating slide 32, opening into the cut-out portion 39, are in register with the edge portions 27 of the valve housing 20.

Accordingly, with the operating slide 32 in said first position shown in FIGS. 7 and 8, and with the slide valve housing 20 inserted in the recess 24 in the coupler housing 25, the slide valve member 28 closing off the through passage 21 therein, the operating slide 32 can be displaced manually at the finger rest 33 to the left, as seen in FIG. 8. The slide valve 28 received by cut-out portion 29 thus is displaced in the reentrant groove 26 to the left, away from port 23, the aperture 34 at the same time being brought into register with the port 31 of the passage 29 in the coupler housing 25, and with the port 23 of the passage 21 in the slide valve housing 20. Thus, when the operating slide has reached the second position thereof, shown in FIG. 9, fluid flow communication is established through the slide valve and coupler assembly.

During the displacement of the operating slide 32 from the first position shown in FIGS. 7 and 8 to the second position shown in FIG. 9, the edge portions 27 at the reentrant groove 26 in the slide valve housing 20 are received in the longitudinal side grooves in the operating slide 32, and by the engagement between the coupler and the slide valve housing thus provided, the slide valve housing will be retained in the position shown in FIG. 9, received by the recess 24.

When the fluid flow connection thus provided is to be interrupted, the operating slide 32 is returned manually to the first position shown in FIGS. 7 and 8, by pulling the operating slide at the finger rest 33 to the right, as seen in FIG. 8. This closes off both the port 31 by the operating slide and the port 23 by the valve member 28, which is returned to the original closed position in the reentrant groove 26. At the same time, the operating slide 32 is disengaged from the edge portions 27 at the side grooves 40. It is now possible to withdraw the slide valve housing 20 from the recess 24, carrying with it the slide valve member 28, and this operation can be performed without leakage or spillage.

The connection and disconnection of the slide valve to and from the coupler can be accomplished without exposure to the atmosphere, or contaminating a sterile environment, since no parts or surfaces of the assembly in contact with fluids passing therethrough are exposed to the atmosphere. Also, no contamination will be transferred from the atmosphere to the line or passage controlled by the assembly.

As shown in FIG. 8, a check valve 41 prevents back flow through the passage 29, and comprises a bushing 42 of plastic material held in the passage 29 by a press-fit, or by bonding with adhesive or by ultrasonic welding. The valve member 43 integral with the bushing 42 is connected therewith by a flexible web 44 allowing the valve member 43 to pivot between the open position shown in FIG. 8 and the closed position against the lower annular end surface of the bushing, and into which position it is brought by fluid pressure or flow through the bushing, and thus prevents back flow through the passage 29.

The coupler housing 25 is connected at the portion 45 to a piece of tubing 46 such as a plastic hose in a snug leak-tight fit, and this tubing links passage 29 at one end with the outlet end coupling 48 of a catheter partly shown in FIG. 6 via a conventional adapter 47. The catheter is introduced in the usual manner into the urethral tube of a patient.

Normally, the operating slide 32 of the slide valve and coupler assembly is in the closed position shown in FIGS. 7 and 8, and no slide valve A is connected to the coupler B. The urine thus will be collected in the patient's bladder, but will not be discharged therefrom until the operating slide 32 is manually displaced to the open position shown in FIG. 9. Preparatory to this being done, a slide valve is removed from its sterile package and attached to the coupler housing in the manner described above. The slide 32 is then opened, and the urine collected in the bladder is discharged in the toilet bowl through the passage 21 at the port 22. This discharge can be carried out hygienically. The slide 32 can be manipulated in an almost natural way during the discharge of urine. Then, the operating slide 32 is closed, and the slide valve A disconnected from the coupler housing and thrown away.

The slide valve and coupler assembly can thus be used in this way to exercise the bladder and restore its flexibility.

In FIG. 11 the tubing 46 connecting the coupler housing 25 with the catheter coupling 48 is a flexible rubber or plastic hose of considerable length. The slide valve housing 20 is permanently connected to or forms part of a conventional plastic bag receptacle 49, which can be suspended at the patient's bed, or can be carried around by the patient. Normally, the receptacle 49 is connected to the catheter coupling 48 by the slide valve and coupler assembly of the invention in the manner previously described, and when the receptacle is full, it can be replaced hygienically by an empty receptacle as described.

It is also possible to interpose a urine measuring container 50 between the catheter coupling 48 and the receptacle 49 by using two slide valve and coupler assemblies of the invention, as shown in FIG. 12. In that case, one assembly A1, B1 is used for coupling the catheter to the inlet in the lid 51 of the measuring container 50, the inlet being formed by the slide valve A1 of that assembly. The outlet 52 of the container 50 is connected to a second slide valve and coupler assembly A2, B2 for connecting the container 50 to the receptacle 49. When the catheter is connected to container 50 through slide valve A1, the outlet 53 is closed by means of the coupler B2, and the receptacle 49 is disconnected therefrom so that the urine will be continuously collected in the container 50, where the volume can be measured. During the collection of the urine, the container is vented through a sterile filter 53. From time to time the urine collected in the container 50 is discharged from the container into the receptacle 49 by connecting the receptacle to the container 50 via the coupler assembly A2, B2.

When receptacle 49 of FIGS. 11 and 12 has been filled with urine, and has been disconnected from the coupler housing 25, it is completely closed off by means of the slide valve and therefore can be handled by the personnel in the hospital without the risk of bacteria being transferred therefrom, because the valve member 28 has been moved to the closed position by means of the operating slide 32, without being wetted by urine on the exterior sides thereof.

FIG. 13 shows an apparatus for emptying a receptacle 49. This apparatus comprises a tub 54 having a beaded rim 55, to which is attached a frame including a flat metal bar 56 extending between two opposite walls of the tub and engaging the rim 55. A rod 57 has two vertical portions connected to the bar 56, and a horizontal portion extending in parallel with the bar spaced upwardly therefrom. On the rod 57 a plurality of spring-clips 58 are arranged for suspending the filled receptacles 49 upside down, and on the bar 56 a plurality of couplers A of the type described above are secured. The passage 29 of each coupler housing is connected to a tubing 59 opening into the tub 54. Thus, the slide valve A of each container 49 suspended in the apparatus can be connected to a coupler B for opening the slide valve and hygienically discharging the contents of the receptable into the tub 54. Tub 54 can be connected directly to a drainage or toilet or waste disposal system.

The slide valve and coupler assembly according to the present invention also can be used in carrying and transferring fluids other than body fluids, e.g. sterilized fluids. Illustrative are flushing of the bladder and supplying sterile solution in peritoneal dialysis.

In FIG. 14 a syringe 60 of conventional design has at the outlet a slide valve A of the slide valve and coupler assembly of the invention. By means of the coupler B of the assembly, which is connected to a cathether coupler 48, the syringe 60 can be connected to the catheter for supplying a flushing liquid to the bladder. This liquid can then be withdrawn again from the bladder by means of the syringe. If a check valve preventing back flow through the coupler B is arranged in the passage 29, as described in FIG. 8, this check valve can be held open magnetically, by embedding a magnetic member in the valve member 43, so that the valve member can be attracted into the open position by a permanent magnet brought near to the coupler housing 28.

FIG. 15 shows a mechanical device for holding the check valve open. On the outlet of the syringe 60 is an annular flange 61, and a corresponding flange 62 is provided on a connector piece 63 adapted to be connected with the slide valve housing 20. A reciprocable tube 64 integral with the flange 61 and projecting therefrom extends through the connector piece 63, and terminates in a pointed end 65. A flexible bellows 66, e.g. of a thin rubbery material, is connected to the flanges 61 and 62 by means of clamp rings 67 and 68, respectively. When the slide valve has been connected to the coupler in the manner previously described, and the valve member 38 has been displaced for opening the passage 21 through valve housing 20, the tube 64 can be axially displaced through the fluid flow passage extending through the open slide valve and coupler assembly, so as to engage the valve member 43, and hold it back so that it cannot close. The flushing liquid supplied by means of the syringe 60 then can be delivered through the tube 64 to the passage 29 upstream of the check valve.

In order to further decrease the likelihood of transfer of bacteria from the slide valve to the passage 29 of the coupler, and the tubing or other conduit connected therewith, the device shown in FIG. 16 can be used. This embodiment inhibits transfer of any bacteria on the outside of the valve housing 20.

In FIG. 16 the operating slide is shown in the closed lefthand position, and is opened by pulling the operating slide to the right by the finger piece 33. This arrangement may be preferred for slide valve and coupler assemblies whose normal position is closed, while the arrangement shown in FIGS. 6 and 15 may be preferred for slide valve and coupler assemblies whose normal position is open.

An inside annular groove 69 in the recess 24 formed by the coupler housing 25 receives a ring 70 of a porous or similar material in which a liquid disinfectant is absorbed. The ring 70 fills recess 24, and the opening formed by the ring is smaller than the recess, so that the ring projects inwardly from the inside surface of the recess. Accordingly, when the valve housing 20 is inserted into the recess 24, it will slide against the ring 70, and the outside surface of the valve housing will be wetted with the disinfectant. Moreover, the ring 70 forms a bacteria barrier in the recess when the valve housing 20 is inserted therein. Other disinfecting means sliding against the outside of the valve housing may be arranged.

Another embodiment for the same purpose is shown in FIGS. 17 and 18. A thin sleeve 81 of flexible material such as rubber is fixed to the outside of the valve housing 20 at 82, and extends over that surface to the end face of the valve member 28. The recess 24 forms an inside shoulder 83, and when the valve housing 20 is inserted into the recess and the valve member received in the cut-out portion 39, the sleeve 81 engages the shoulder 83, and thus will be held back in displacement of the housing 20 as shown in FIG. 18. Therefore, the valve housing 20 will move in relation to the sleeve 81. The outside surface of the housing effectively covered by the sleeve is partially uncovered when the housing 20 is finally displaced to the position for locating the valve member 28 in the cut-out portion 39. Thus, the sleeve 81 forms an efficient protection against contamination of the exterior side surfaces of the valve 28.

FIGS. 19 to 22 show a further preferred embodiment of the slide valve and coupler assembly according to the present invention.

The operating slide 32' has a second cut-out portion 39' with a second valve member 28' on the opposite side of aperture 34.

The gasket 37 of FIGS. 7 to 9 is replaced by a sealing plate 37' of a resilient material such as rubber or plastic. The operating slide 32' can be displaced from a first position, shown in FIGS. 19 and 20, when the valve housing 20 is inserted in the recess 24, to a second position shown in FIG. 21, wherein the passage through the assembly is established, and finally to a third position, shown in FIG. 22, wherein the second valve member 28' closes off the opening through the valve housing 20. In this third position the valve housing 20 can be removed from the coupler housing 25 with the slide valve member 28' attached.

The slide valve and coupler assembly according to the invention can be used for peritoneal dialysis. In that case, the slide valve is attached to the catheter leading to the abdominal cavity, and is connected by means of the coupler to a plastic bag containing the sterilized solution, or to an apparatus for delivering such sterilized solution.

The slide valve and coupler assembly shown in FIGS. 19 to 22 is used when there is a rigorous requirement for a sterile environment during connection and disconnection of the coupling members. The operating slide 32' and the coupler housing 25 accordingly are used only once, to ensure the maintenance of a sterile environment. The slide valve A with valve member 28 and the coupler B with valve member 28' can be packaged before use within sterile housings or covers.

This slide valve and coupler assembly can be used with any desired receptacle of fluid supply. The operating slide is placed in said three positions by a resilient arm 85 formed integrally with the finger piece, and extending along the operating slide spaced therefrom, and having a projecting detent 85a that resiliently engages one of three notches 86 in this coupler housing corresponding to each of the three positions, of which two are shown at 86, but can be disengaged manually therefrom when it is desired to move the operating slide to another position.

Preferably the slide valve and coupler assembly is made of nontoxic material that is inert to the fluid with which they come into contact. They can be of metal or plastice, e.g., aluminum, stainless steel, polypropylene, polyethylene, polyvinyl chloride, polyamide, polytetrafluoroethylene, polycarbonate, poloxymethylene, polyvinylidene chloride, natural and synthetic rubbers, polystyrene, and urea-formaldehyde and melamine-formaldehyde resins.

While not essential, if desired, a filter can be included in either or both of the slide valve housing and coupler housing, disposed across the fluid flow passage therethrough.

In order to further inhibit transfer of bacteria, an absorbent material can be provided on the lower face of the operating slide 32, in a recess formed in the operating slide between the cut-out portion 39 and the through opening 34, so that a liquid disinfectant absorbed by the material will wet the end surface of slide valve housing 20 when the valve member 28 is displaced from the closed position of FIG. 7 to the open position of FIG. 9.

In the embodiments described, the operating means comprises a displaceable slide, but it is also possible to arrange such means as a rotatable body in the coupler housing 25.

Having regard to the foregoing disclosure, the following is claimed as patentable and inventive embodiments thereof:

1. A slide valve and coupler assembly for controlling flow in one line when attached only to that line and for controlling flow in a fluid line correction between two lines when coupled between those two lines, comprising, in combination,
(a) a slide valve comprising:
  (1) a valve housing having a fluid inlet and a fluid outlet and means for attaching a first line to one of the inlet and outlet;
  (2) a first fluid flow passage through the housing between the fluid inlet and the fluid outlet;
  (3) at least one slide valve member;
  (4) guide means in the housing for guiding the slide valve member into a position across and closing off the passage to fluid flow and away from that position, leaving the passage open so that fluid flow can proceed past the valve;
  (5) the slide valve member being carried on and reciprocable into and away from said closed position along said guide means; and
(b) a coupler comprising:

(1) a coupler housing having a fluid inlet and a fluid outlet and means for attaching a second line to one of the inlet and outlet;

(2) a second fluid flow passage through the coupler housing between the fluid inlet and the fluid outlet;

(3) a first recess for receiving at least the slide valve member-containing portion of the slide valve housing; the first flow passage through the valve housing and the second flow passage through the coupler housing being in alignment when the valve housing is in the first recess;

(4) at least one second recess abutting and beside the first recess, receiving the slide valve member in a position away from the flow passage through the slide valve housing;

(5) operating means for sliding the slide valve member, when the valve housing is inserted in the first recess, between said positions across and closing off the flow passage through the assembly, and away from and opening the flow passage through the assembly; and (6) retaining means on said operating means connecting with the valve housing when the operating means is operated to slide the slide valve member to said opened position; and retaining the slide valve to the coupler;

whereby the slide valve member controls flow in the first line when the slide valve housing is attached only to that line, and controls flow in the first and the second lines when the slide valve housing is inserted in the first recess of the coupler, and the assembly is attached to the first and second lines.

2. A slide valve and coupler according to claim 1 in which the operating means in the coupler for sliding the valve member between the said positions is an operating slide movable between positions across and away from the second flow passage through the coupler housing.

3. A slide valve and coupler according to claim 1 in which the valve housing is shaped with a reentrant slot serving as a track for the slide valve member, along which the valve member can be slid between positions across and away from the first fluid flow passage, and the reentrant portion retains the valve member closely against the inner face of the housing with a sealing element, sealing or action therebetween.

4. A slide valve and coupler according to claim 3 in which the operating means in the coupler for sliding the slide valve member between the said position is an operating slide movable between positions across and away from the second flow passage through the coupler housing.

5. A slide valve and coupler according to claim 4 in which the inner face of the coupler housing is channel-shaped, with sides defining a recess for reception of the operating slide.

6. A slide valve and coupler according to claim 5 in which a sealing element is interposed between the inner face of the coupler housing at the recess and the adjoining face of the operating slide.

7. A slide valve and coupler according to claim 6 in which the operating slide has finger rests at each end, for manual pushing of the slide along the recess, and peripheral grooves forming said locking means on its sides which engage edge portions of said reentrant slot in the valve housing.

8. A slide valve and coupler according to claim 4 in which the operating slide has an aperture corresponding in dimensions and open area to the first and second fluid flow passages of the valve and coupler housings, and when the aperture is in register with the passages the passages are open and interconnected for fluid flow, and when it is not, the passages are closed.

9. A slide valve and coupler according to claim 4 in which the ends of the operating slide project from the housing on each side of the recess and the projecting portions are covered by flexible covers attached to each side of the housing over the recess, inhibiting entry of contaminants into the recess.

10. A slide valve and coupler according to claim 1 in which the operating means in the coupler for sliding the slide valve member between the said positions is an operating slide movable between positions across and away from the second flow passage through the coupler housing; the valve housing is shaped with a reentrant slot serving as a track for the slide valve member, along which the valve member can be slid between positions across and away from the first fluid flow passage, and the reentrant slot retains the valve member closely against the inner face of the housing with a sealing element therebetween; the inner face of the coupler housing is channel-shaped, with sides defining a recess for reception of the operating slide; a sealing element is interposed between the inner face of the coupler housing at the recess and the adjoining face of the operating slide; the operating slide has finger rests at each end, for manual pushing of the slide along the recess, and peripheral grooves forming the locking means on its sides which engage edge portions of the reentrant slot in the valve housing; the operating slide has an aperture corresponding in dimensions and open area to the first and second fluid flow passages of the valve and coupler housings, and when the aperture is in register with the passages the passages are open and interconnected for fluid flow, and when it is not, the passages are closed; and the ends of the operating slide project from the housing on each side of the recess and the projecting portions are covered by flexible covers attached to each side of the housing over the recess, inhibiting entry of contaminants into the recess.

11. A slide valve and coupler assembly according to claim 1 in which the slide valve forms part of a receptacle or container 12.

12. A slide valve and coupler assembly according to claim 1 in which a check valve is provided in the second flow passage of the coupler.

13. A slide valve and coupler assembly according to claim 12 having means for moving the check valve to an open position.

14. A slide valve and coupler assembly to claim 13 in which the means for moving the check valve comprises a tube displaceable through the coupler housing into the second flow passage of the coupler into contact with the check valve to move it to an open position.

15. A slide valve and coupler assembly according to claim 1 having disinfecting means in the wall of said first recess.

16. A slide valve and coupler assembly according to claim 1 having a flexible sleeve enclosing the slide valve member and connected to the slide valve housing at a position spaced from the slide valve member.

17. A slide valve and coupler assembly according to claim 1 comprising a second slide valve member carried on and reciprocable into and away from a closed position along the guide means and carried by the same guide means as the first slide valve member.

* * * * *